United States Patent
Ikuta et al.

(10) Patent No.: US 10,859,438 B2
(45) Date of Patent: Dec. 8, 2020

(54) ULTRAMINIATURE ENDOSCOPY

(71) Applicant: Canon USA, Inc., Melville, NY (US)

(72) Inventors: Mitsuhiro Ikuta, Cambridge, MA (US); Tzu-Yu Wu, Malden, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 16/751,082

(22) Filed: Jan. 23, 2020

(65) Prior Publication Data

US 2020/0240839 A1     Jul. 30, 2020

Related U.S. Application Data

(60) Provisional application No. 62/797,882, filed on Jan. 28, 2019.

(51) Int. Cl.
*G01J 3/28*     (2006.01)
*G01J 3/02*     (2006.01)

(52) U.S. Cl.
CPC .............. *G01J 3/0218* (2013.01); *G01J 3/28* (2013.01)

(58) Field of Classification Search
CPC .... G01J 3/0218; G01J 3/28; G01J 3/02; G01J 3/0289; A61B 1/00096; A61B 1/07; A61B 1/0638; A61B 1/00172; A61B 1/00188; A61B 1/00167; A61B 1/00; A61B 5/0084; G02B 23/2423; G02B 23/26
See application file for complete search history.

(56) References Cited

U.S. PATENT DOCUMENTS

| | | | |
|---|---|---|---|
| 2008/0205833 A1* | 8/2008 | Fu | A61B 5/0062 385/117 |
| 2018/0017778 A1 | 1/2018 | Ikuta et al. | |
| 2018/0120555 A1 | 5/2018 | Ikuta et al. | |

FOREIGN PATENT DOCUMENTS

WO     2017/139657 A1     8/2017

* cited by examiner

*Primary Examiner* — Abdullahi Nur
(74) *Attorney, Agent, or Firm* — Canon U.S.A., Inc. IP Division (57) ABSTRACT

A spectrally encoded endoscopy optical device includes a bundle of multi-mode optical fibers that transmits light received from an imaging target to a spectrometer. A far field pattern of light transmitted through a fundamental mode of at least one of the multi-mode optical fibers is nonparallel to an optical axis of the spectrometer for reducing nonuniformity of the far field pattern at an input sensor of the spectrometer. For still further reduction of such nonuniformity, a far field pattern of light transmitted through a fundamental mode of the bundle of multi-mode optical fibers is nonparallel to an optical axis of the spectrometer.

14 Claims, 13 Drawing Sheets

ULTRAMINIATURE ENDOSCOPY

BACKGROUND

Field of the Disclosure

The present disclosure generally relates to endoscopy and, more particularly, to ultraminiature endoscopes and ultra ultraminiature endoscope probes having enhanced light coupling efficiency.

Description of the Related Art

Spectrally encoded endoscopy (SEE) probes are known that generate spectrally-encoded illumination using probe illumination optics having a grating disposed toward a target. The probes detect light reflected from the target through a plurality of detection optical fibers. The detection optical fibers surround illumination optics. To cover a field of view of the illumination and obtain large amount of reflected light, high numerical aperture (NA) multi-mode optical fibers (about 0.5 or higher) are used as the detection optical fibers. The detection optical fibers are connected to a spectrometer, and the detected light spectrum is measured and analyzed.

Spectrally encoded endoscopy (SEE) probes are known also that have a plurality of detection optical fibers. For example, FIG. 14 of U.S. Patent Publication No. 2018/0017778 A1 discloses an embodiment of SEE probe that has a plurality of detection optical fibers. Moreover, FIGS. 9 and 10 of U.S. Patent Publication No. 2018/0017778 A1 disclose an embodiment of SEE probe wherein detection optical fiber tips are angle-polished to increase a field of view of endoscopic detection.

SUMMARY

According to an aspect of the present disclosure, a spectrally encoded endoscopy optical device includes a bundle of multi-mode optical fibers that transmits light received from an imaging target to a spectrometer. A far field pattern of light transmitted through a fundamental mode of at least one of the multi-mode optical fibers is nonparallel to an optical axis of the spectrometer for reducing nonuniformity of the far field pattern at an input sensor of the spectrometer.

According to another aspect of the present disclosure, for still further reduction of such nonuniformity, a far field pattern of light transmitted through a fundamental mode of the bundle of multi-mode optical fibers is nonparallel to an optical axis of the spectrometer.

Further features of the present disclosure will become apparent from the following description of exemplary embodiments with reference to the attached drawings.

DESCRIPTION OF THE EMBODIMENTS

Various exemplary embodiments, features, and aspects of the disclosure will be described with reference to the drawings. According to an aspect of the present disclosure, multi-mode optical fibers can be used for detection optics of a SEE probe. According to another aspect of the present disclosure, light reflected from a target is coupled to the multi-mode optical fibers and is delivered to a spectrometer. According to yet another aspect of the present disclosure, in optics between a distal end of the optical fibers and a spectrometer aperture, an optical axis of one part of the optics is tilted relative to an optical axis of a next part, so that throughput for light from a large view angle is increased while throughput for light from a small view angle is decreased. To facilitate a fuller understanding of these and other aspects of the present disclosure, a comparative example which details various aspects of bundled multi-mode optical fibers in a SEE probe is discussed next with reference to FIGS. 1A and 1B.

Figure 1A:
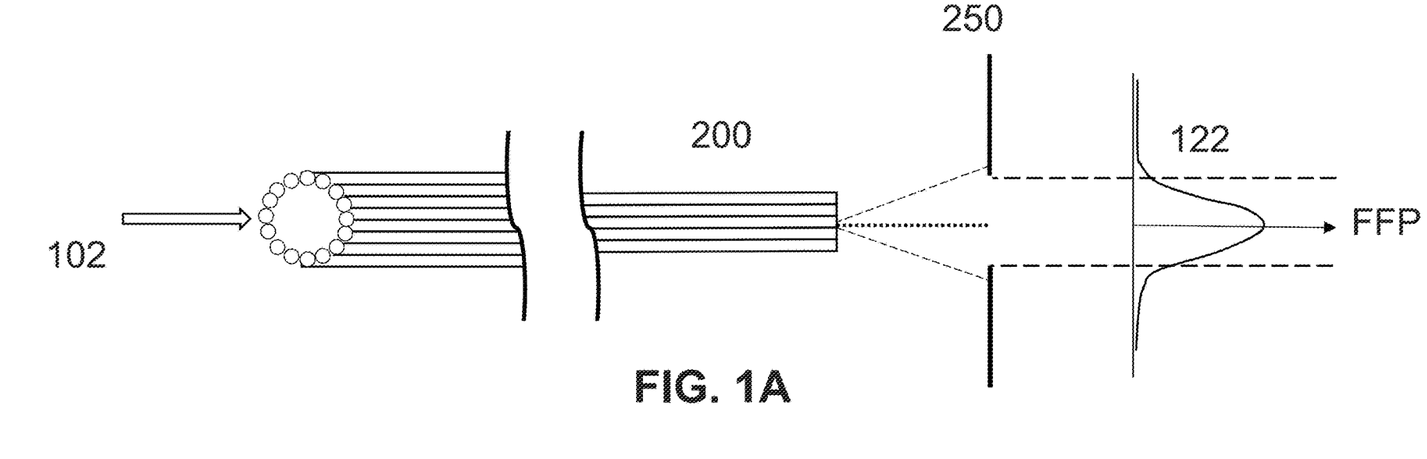
FIGS. 1A and 1B are schematic views of a comparative example to illustrate an issue addressed by various embodiments of the present disclosure.
Figure 1B:
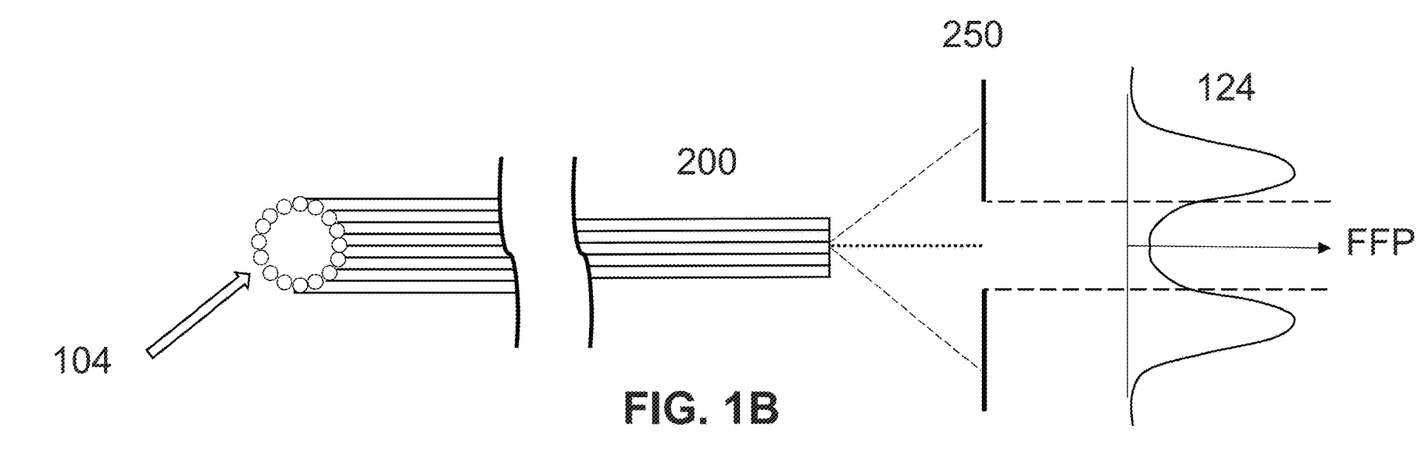

Referring now to FIGS. 1A and 1B, there are shown schematic views of a comparative example to illustrate an issue addressed by various embodiments of the present disclosure. Multi-mode optical fibers can deliver light over a plurality of modes. Usually low-angle incident light 102 couples to optical fiber in low-order modes whereas high-angle incident light 104 couples in high-order modes. Some mode-mixing happens inside of the optical fiber. However, light entering the optical fiber in a low-order mode mostly remains in the low-order mode at the other end of the optical fiber, and light entering the optical fiber in a high-order mode typically remains in the high-order mode at the other end of the optical fiber.

When the other end of each of the optical fibers 200 has a respective normal that is parallel to its respective optical fiber axis, a far field pattern (FFP) 122 at a sensor end (sensor not shown) has a center-peak shape for light with low incident angle as shown in FIG. 1A, whereas the FFP 124 at the sensor end is larger for higher order modes and can have a non-single peak shape such as a ring shape (e.g. the light intensity peak is not at center) as shown in FIG. 1B.

Light with large FFP for which intensity at center is low can suffer a large amount of vignetting at a spectrometer aperture (represented as entrance spectrometer entrance pupil 250 in FIG. 1). The light outside of the spectrometer entrance pupil 250 (which is determined by spectrometer optical components such as aperture 240, lenses 222, 226 and a grating 224) cannot be detected by a sensor of the spectrometer appropriately, which causes poor image quality (large noise) for large view angle area in SEE imaging due to low signal intensity.

Coupling efficiency from imaging sample to detection optical fibers depends on incidence angle at the optical fiber ends. When an optical axis of an optical fiber is normal to the optical fiber end, coupling efficiency is usually largest at a 0-degree angle of incidence (relative to normal) and low at high angle of incidence (relative to normal). Accordingly, the coupling non-uniformity and vignetting at the spectrometer discussed above degrades image quality for large view angle areas.

Figure 2:
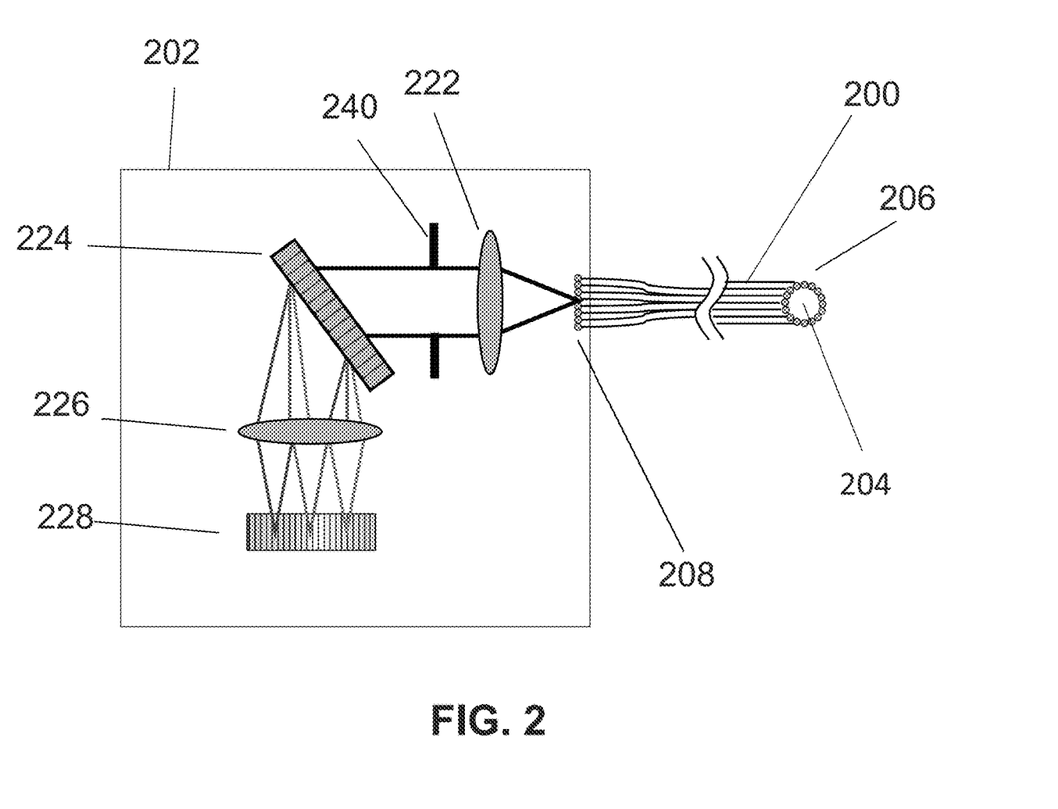
FIG. 2 is a schematic image of SEE detection optics having an optical fiber tilt feature in accordance with a first example embodiment of the present disclosure.

Referring now to FIG. 2, there is shown a schematic image of SEE detection optics having an optical fiber tilt feature in accordance with a first example embodiment of the present disclosure. Detection optical fibers 200 are connected to a spectrometer 202. The spectrometer 202 includes a collimation lens 222, a diffraction grating 224, an imaging lens 226, and a sensor 228. The sensor 228 can be a CCD line sensor, for example. As an example, in this embodiment, the focal length of collimation lens 222 is 120 mm, groove density of the diffraction grating 224 is 1260 lines/mm, and focal length of the imaging lens 226 is 55 mm. The angle of incidence to the grating 224 is accordingly 19.3 degrees, and the length of active area of the sensor 228 is 12 um/pixel×2048 pixel=24.576 mm. The above is merely a configuration example, and other densities and dimensions are also possible.

At the distal end 206 of the optical fibers 200, the detection optical fibers can surround space for SEE illumination optics 204. For example, the optical fibers 200 can be bundled as ring shape. The distal end 206 of the detection optical fibers 200 serves as an input of the SEE optical probe.

At the proximal end 208, which is at the entrance of the spectrometer 202, the detection optical fibers 202 can be bundled as rectangular shape. The width and height of the rectangular shape can be optimized for spectrometer resolution and magnification. The detection optical fibers 200 can be, for example, multi-mode optical fibers having numerical aperture (NA) of 0.2 or higher. Preferably the NA of the optical fibers is 0.5 or higher to detect light incidence at large incidence angles. The detection optical fibers 200 can be step-index or graded index optical fibers. The core diameter can be larger than 10 um, for example, 30, 50, 70, 90, or 120 um. Preferably, the number of the detection optical fibers 200 is more than one. As examples, the number of the detection optical fibers 200 can be, but is not limited to, 10, 20, 30, 45, 60, 120, or 240.

For example, 45 multimode optical fibers 200 with 68 um core diameter, 70 um clad diameter, and 0.66 NA can surround a tubing (980 um outer diameter, 750 um inner diameter) which contains circular space for SEE illumination optics 204. The optical fibers 200 can be bundled as rectangular shape (15 rows×3 columns) at the proximal end 208. In this example, the spectrometer 202 has lateral magnification of 0.45× and the pixel height of the sensor 228 is 500 um. Accordingly, the image height of the rectangular optical fiber bundle will be about 70×15×0.45=472.5 um, which is smaller than the sensor height 500 um (the pixel height 500 um of the sensor 228).

The spectrometer 202 has at least one optical aperture stop 240. The aperture stop 240 can be provided by a physical aperture, or a clear aperture of any optical component in the spectrometer 202. The aperture stop can be any shape such as rectangular or oval. The spectrometer 202 has an entrance pupil, which is an image of the aperture stop seen through the front of the spectrometer optics (from the detection optical fibers side). Based on the entrance pupil, the spectrometer has an acceptance angle range. That means that when light from the optical fibers 200 is outside of the acceptance angle range, the light cannot be accepted to the spectrometer 202. For example, the angle range may be from −11.5 degrees to +11.5 degrees (0.2 in numerical aperture).

As can be seen in FIG. 2, the optical axis of the spectrometer 202 in the first example embodiment changes direction at the grating 224, and the same is true for the further example embodiments discussed below, although for the sake of clarity in the drawings discussed below the optical axis of the spectrometer 202 is shown as a straight line, as such makes it easier to understand the structure and operation the spectrometer 202, and in particular, makes it easier to understand how light trajectories through the spectrometer and light densities at the sensor 228 are affected.

Figure 3:
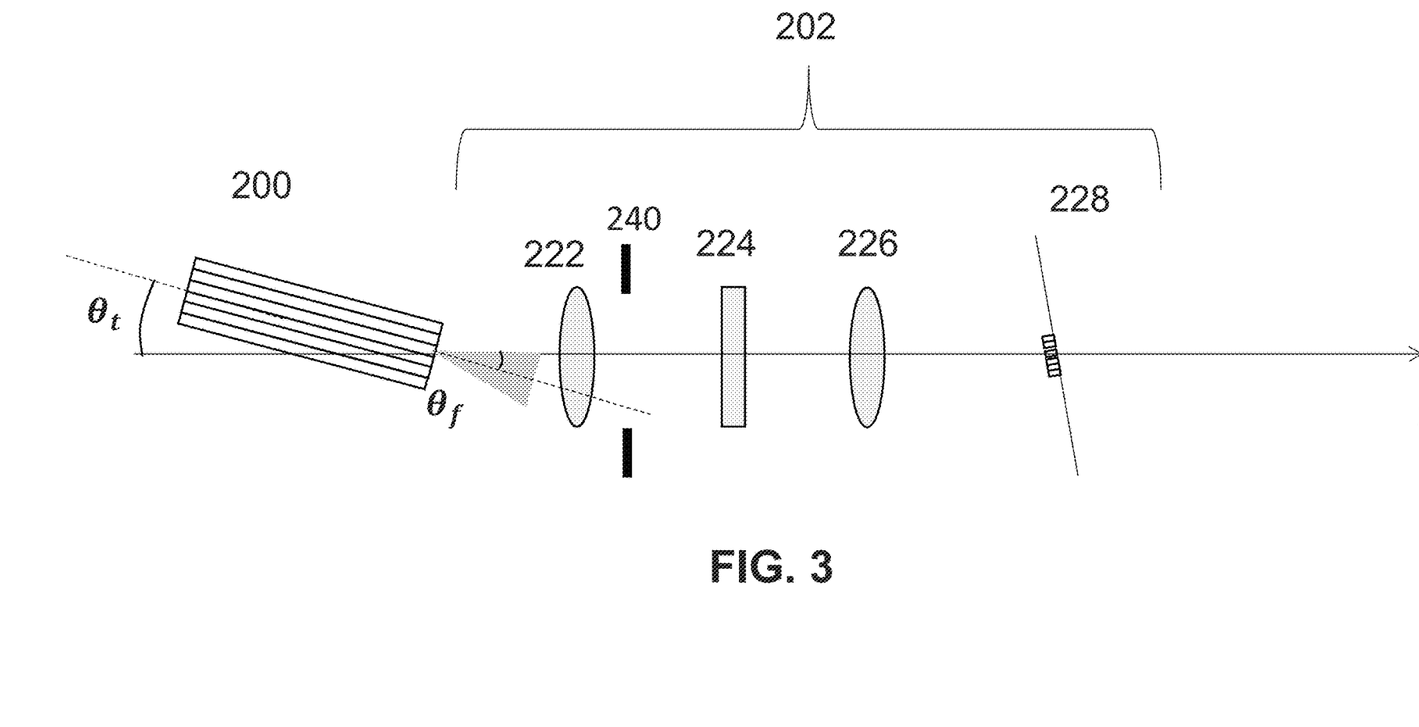
FIG. 3 is an exploded partial view of the first example embodiment of the present disclosure.
Figure 4A:
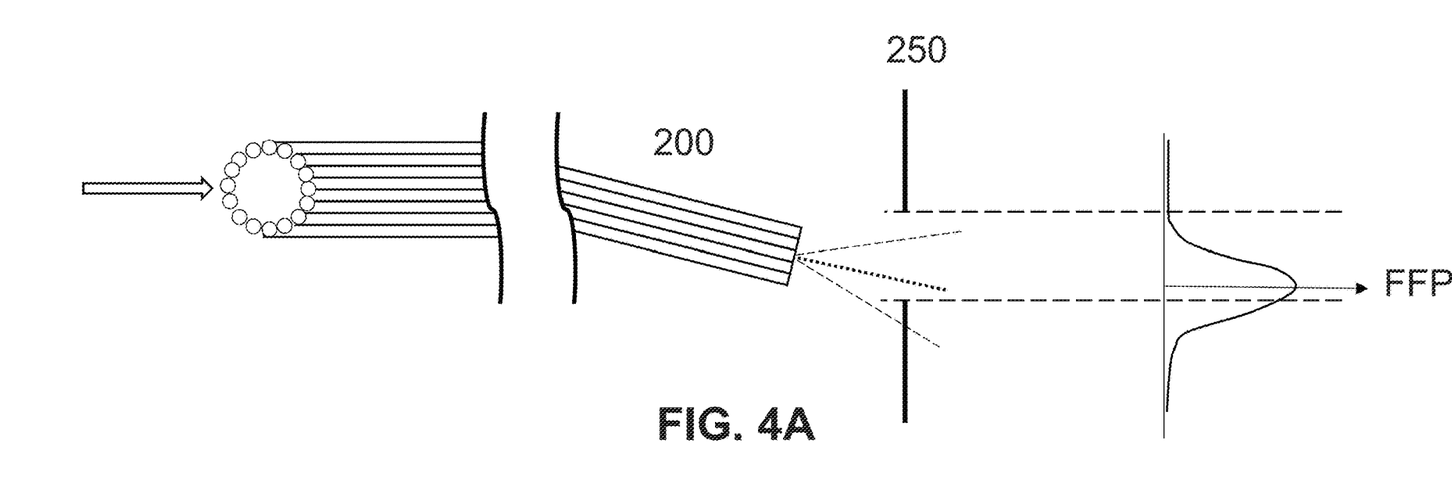
FIGS. 4A and 4B are additional exploded partial views of the first example embodiment of the present disclosure.
Figure 4B:
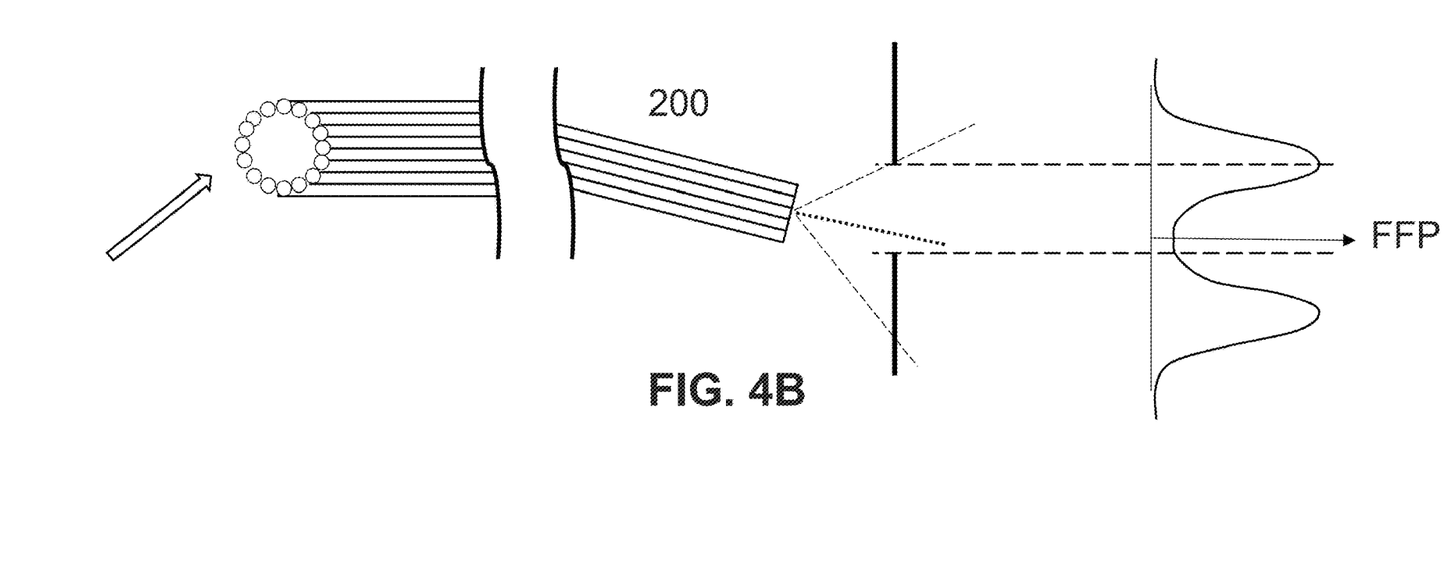

Referring now also to FIGS. 3, 4A and 4B, there are shown exploded partial views of the SEE detection optics in accordance with the first example embodiment. The bundle of detection optical fibers 200 is tilted at an entrance of the spectrometer 202 as shown in FIGS. 3, 4A and 4B. The FFP peak direction of light delivered through the fundamental mode of the bundle of detection optical fibers 200 is not parallel to optical axis of the spectrometer 202 at the spectrometer entrance. The tilted axis can be in the same plane as the groove direction of the grating 224 so that tilting does not affect relation between wavelengths of light and pixel indices of the sensor 228.

In this configuration, a far field pattern (FFP) of the light from the optical fibers 200 is shifted (tilted) relative to the entrance pupil 250 of the spectrometer 202 as shown in FIG. 4. The FFP tilt angle $\theta_f$ can be calculated by expression Ex. 1 shown below $$\theta_f = \theta_t \qquad (\text{Ex. 1}),$$

wherein $\theta_t$ is an optical fiber tilt angle relative to an optical axis z of the spectrometer 202, as shown in FIG. 3. As examples, the optical fiber tilting angle can be, but is not limited to, 5 degrees, 10 degrees, or 15 degrees. The sensor 228 can be tilted based on the optical fiber bundle tilt and spectrometer magnification so that image of the optical fibers 200 is in focus at the sensor plane.

Tilting the optical fiber decreases optical throughput from the optical fibers 200 to the sensor 228 for small view angle detection (FIG. 4A), but can increase optical throughput significantly for large view angle detection (FIG. 4B). Since coupling from sample to the optical fibers 200 at the distal end is lower in large view angle detection than that in small view angle detection, tilting the optical fiber is beneficial, for example, for normalizing the signal level throughout the field of view of the SEE optical probe. It is also beneficial to tilt the sensor 228 based on the tilt of the optical fibers 200, (for example, in an opposite direction as the tilt of the optical fibers 200) so that an image of the optical fibers 200 is in focus at the sensor plane, as shown in FIG. 3.

When an aperture 240 that determines the entrance pupil 250 is located after collimation lens 222, shifting optical fiber bundle 200 and collimation lens 222 from optical axis of the rest of the spectrometer components can provide a like effect as that shown in FIG. 13 (discussed below). In this case, $\theta_t$ is optical fiber tilt angle relative to the direction going to the center of entrance pupil; $\theta_f$ is FFP tilt angle relative the direction going to the center of entrance pupil. The FFP tilt angle $\theta_f$ can be calculated using expression Ex. 2 given below $$\theta_f = \sin^{-1}\left(\frac{y}{f}\right), \quad \text{(Ex. 2)}$$

wherein f is focal length of collimation lens and y is lens shift. The optical fiber tilt angle $\theta_t$ can be calculated using expression Ex. 1, that is by $\theta_f=\theta_t$. For example, when focal length of collimation lens 222 is 120 mm, and lens shift is 21 mm, the FFP tilt angle $\theta_f$ is 10.08 degrees, and optical fiber tilt angle $\theta_t$ is 10.08 degrees.

In the following description of further example embodiments, various distinctions are disclosed from the first example embodiment discussed above. To more clearly depict the differences from the first example embodiment, in some instances components of the first example embodiment are not shown or discussed where they are the same as those discussed above with respect to the first example embodiment.

Figure 5:
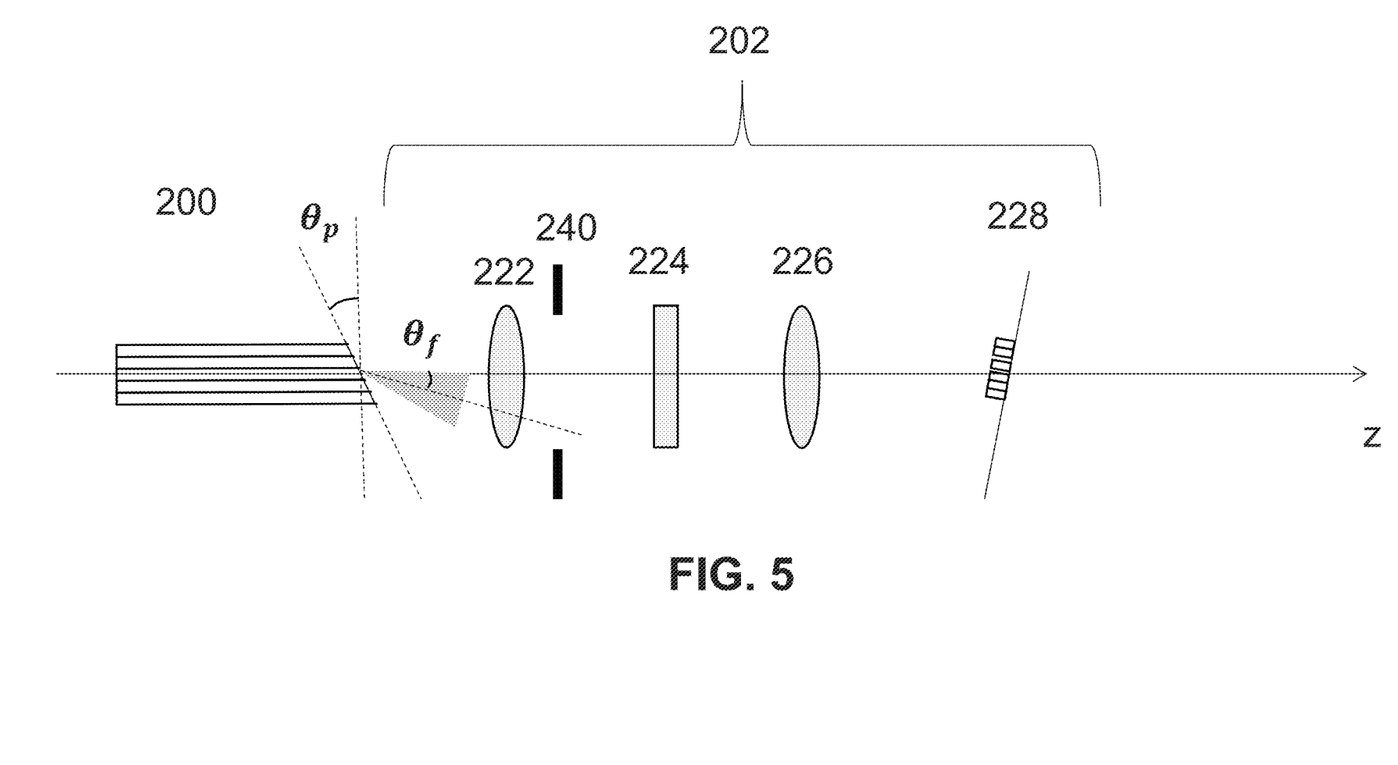
FIGS. 5, 6A and 6B are exploded partial views of SEE detection optics having an optical fiber angle polish feature in accordance with a second example embodiment of the present disclosure.
Figure 6A:
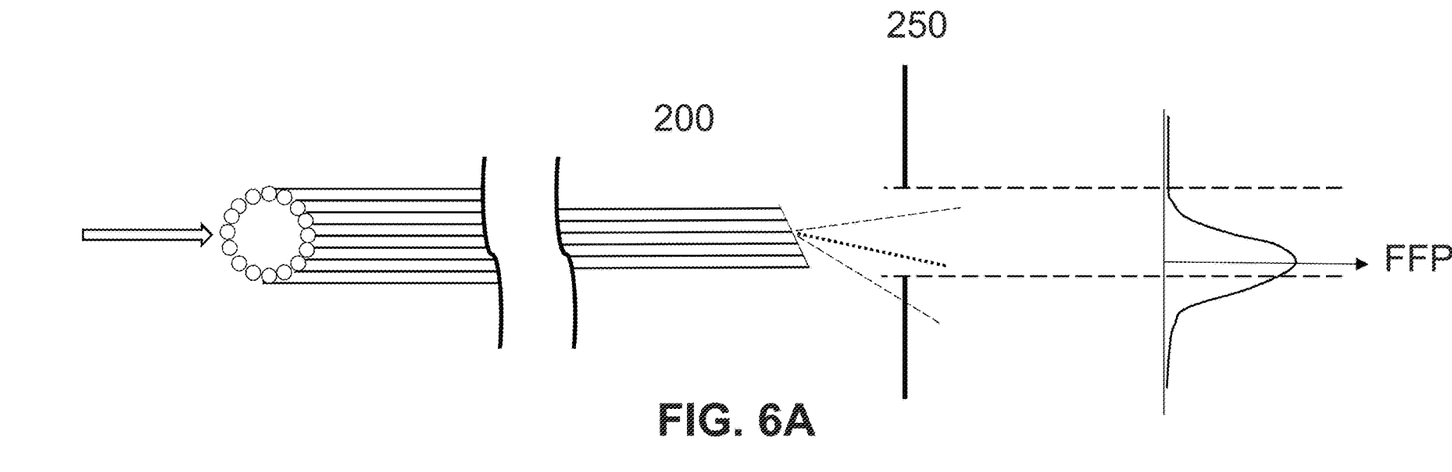
Figure 6B:
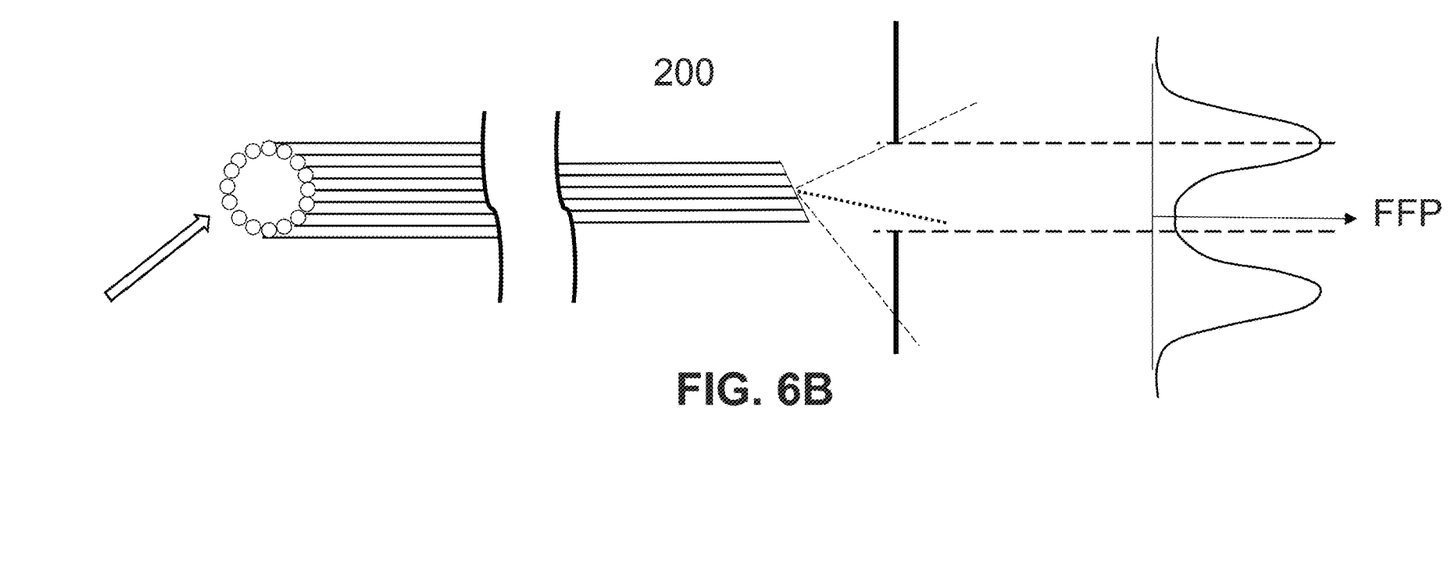

Referring now also to FIGS. 5, 6A and 6B, there are shown exploded partial views of SEE detection optics having an optical fiber angle polish feature in accordance with a second example embodiment of the present disclosure. In the second example embodiment, instead of a tilt feature, the bundle of optical fibers 200 is angle-polished at the entrance of spectrometer 202, as shown in FIG. 5. The FFP peak direction of light delivered through the fundamental mode of the detection optical fiber bundle 200 is not parallel to optical axis of the spectrometer 202 at the spectrometer entrance. The FFP tilt angle $\theta_f$ can be calculated using expression Ex. 3 given below $$\theta_f = \sin^{-1}(n \sin \theta_p) - \theta_p \quad \text{(Ex. 3)},$$

where n is optical fiber core refractive index and angle $\theta_p$ is optical fiber polishing angle. For example, if the optical fiber refractive index is 1.5 and the optical fiber bundle 200 is polished by 20 degrees, the FFP will be tilted by 10.86 degrees. The sensor 228 can be tilted based on the polishing angle of the optical fiber bundle 200 so that an image of the optical fibers 200 is in focus at the sensor plane. An advantage of the second example embodiment is that alignment of the optical fiber bundle in z-direction can be done easily without changing its location in x- and y-directions since optical fiber axis can be parallel to z-direction.

Figure 7:
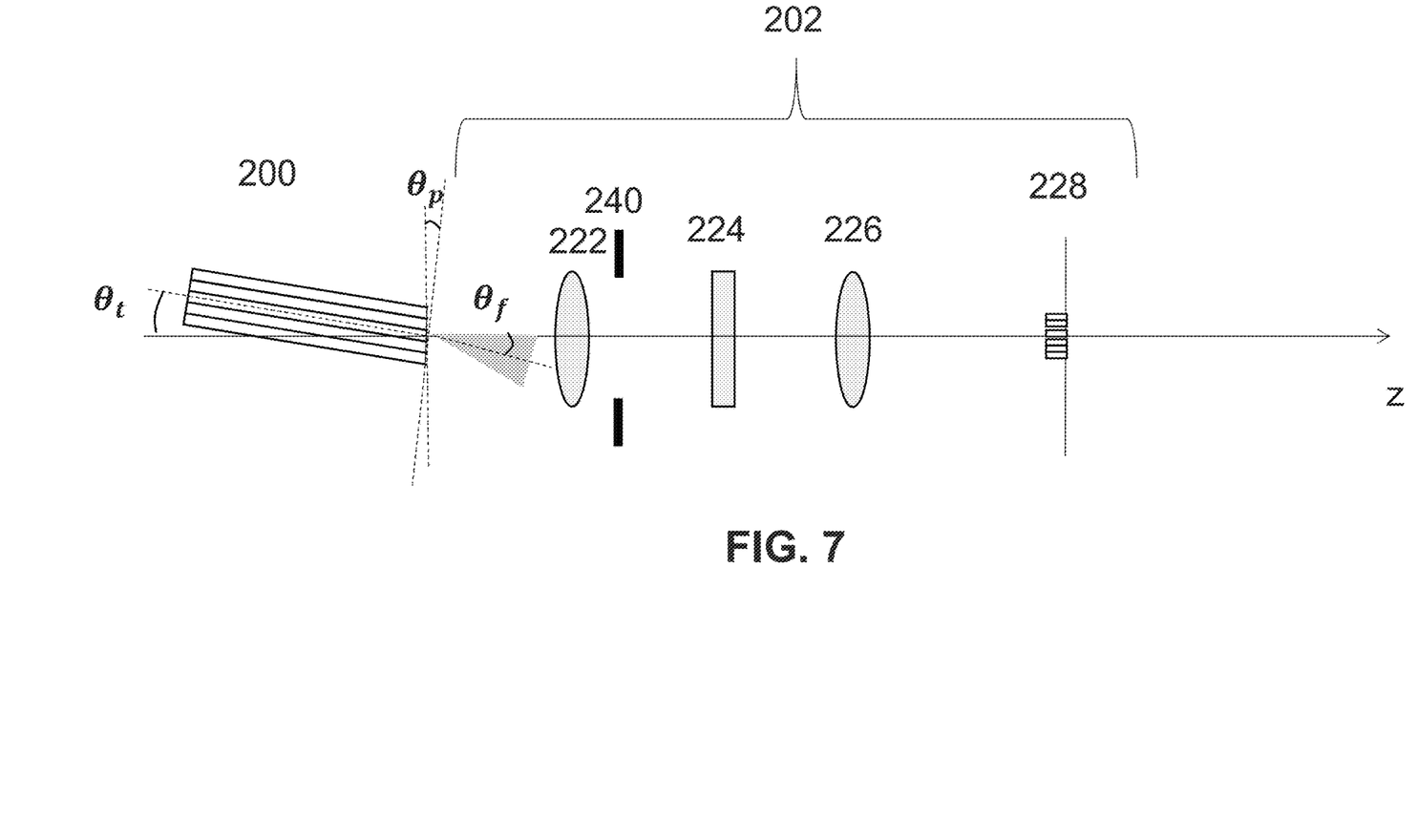
FIGS. 7 and 8 are exploded partial views of SEE detection optics having an optical fiber tilt feature and an optical fiber angle polish feature in accordance with a third example embodiment of the present disclosure.
Figure 8:
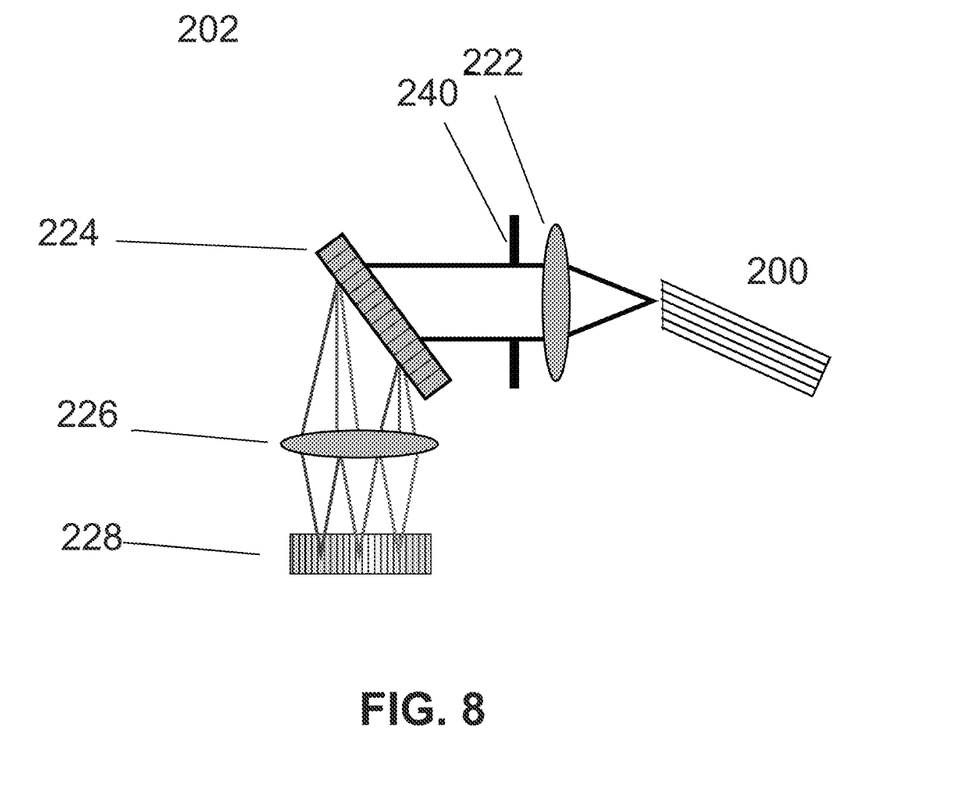

Referring now also to FIGS. 7 and 8, there are shown exploded partial views of SEE detection optics having an optical fiber tilt feature and an optical fiber angle polish feature in accordance with a third example embodiment of the present disclosure. In the third example embodiment, optical fiber bundle tilting and angle polish is combined at the spectrometer entrance. The FFP peak direction of light delivered through the fundamental mode of the detection optical fiber bundle 200 is not parallel to optical axis of the spectrometer 202 at the spectrometer entrance. The FFP tilt angle $\theta_f$ can be calculated using expression Ex. 4 given below $$\theta_f = \theta_t + \sin^{-1}(n \sin \theta_p) - \theta_p. \quad \text{(Ex. 4)}$$

When $\theta_t=\theta_p$, the end of the bundle of optical fiber at the entrance of the spectrometer 202 can be perpendicular to the optical axis (z) of the spectrometer as shown in FIG. 7. Beneficially, in accordance with this configuration, the surface of the sensor 228 can be perpendicular to the spectrometer axis, which makes optical alignment of the spectrometer easier. In this configuration, optical fiber tilting/polishing direction can be not only in vertical direction (non-diffraction direction of the grating 224), but also in lateral direction (diffraction direction) as shown in FIG. 8. For example, if the optical fiber refractive index is 1.5 and the optical fiber bundle 200 is polished by 7 degrees, and tilted by 7 degrees in the same direction, the FFP will be tilted by 10.53 degrees.

Figure 9:
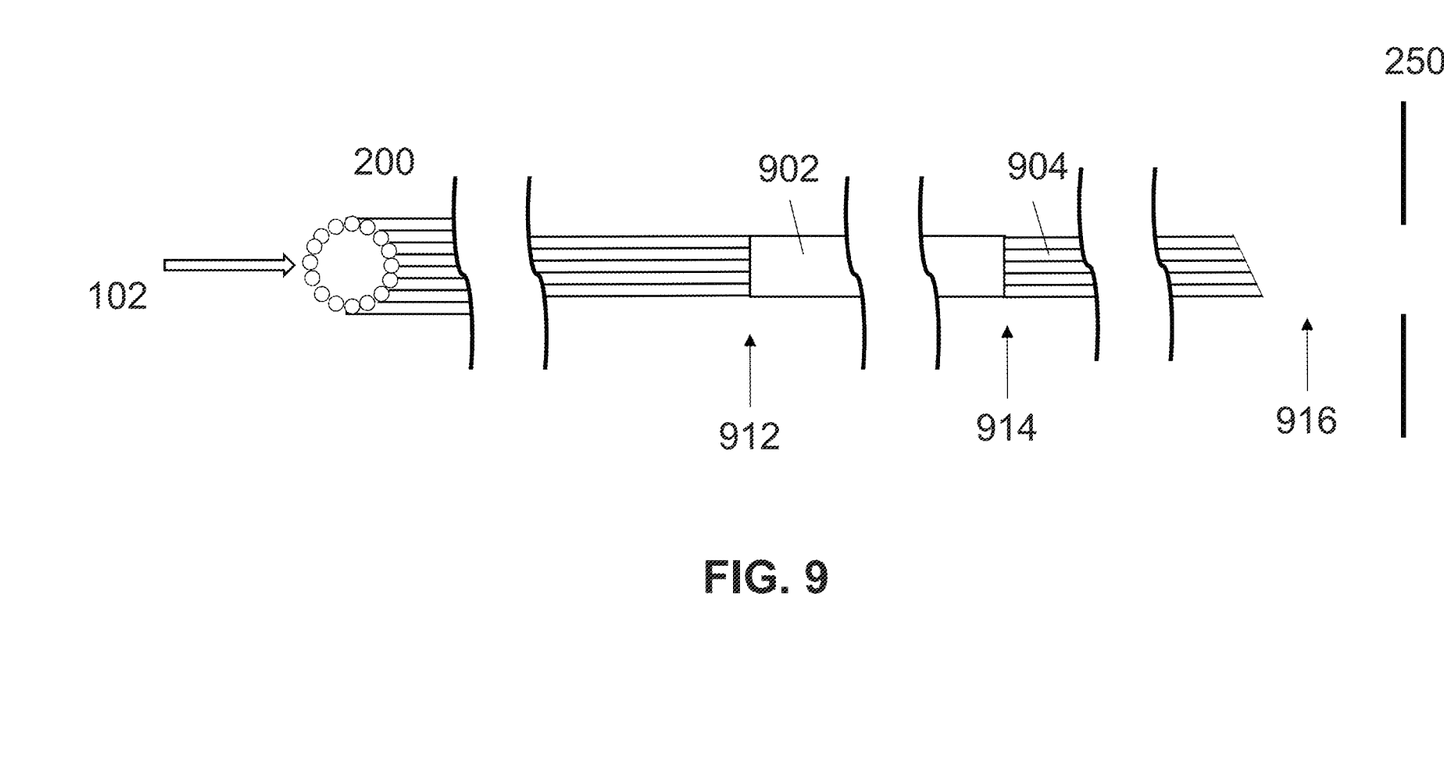
FIG. 9 is an exploded partial view of SEE detection optics having an additional bundle of optical fiber, or a waveguide, disposed between a bundle of detection optical fibers and a spectrometer, according to a fourth example embodiment of the present disclosure.

Referring now also to FIG. 9 there is shown an exploded partial view of SEE detection optics having an optical transmission medium disposed between the bundle of detection optical fibers 200 and spectrometer 202, the optical transmission medium comprising at least one of an additional bundle(s) of optical fiber and a waveguide(s), according to a fourth example embodiment of the present disclosure. For example, as shown in FIG. 9, a waveguide 902 can be attached to the bundle of detection optical fibers 200, and another bundle of optical fibers 904 can have one end attached to the waveguide 902 and another end attached to the spectrometer 202. As one example, the waveguide 902 can be a single core multi-mode optical fiber. As another example, the waveguide 902 can be a bundle of multi-mode optical fibers. The bundle of optical fibers 200 can have, for example, a circular shape at the joint 912 with the waveguide 902. The bundle of optical fibers 904 can have, for example, a circular shape at the joint 914 with the waveguide 902. The bundle of optical fibers 904 can have, for example, a rectangular shape at the spectrometer entrance 916 to control width and height of the shape. The joints 912 and 914 can be, for example, connectorized and detachable. The bundle of optical fibers 904 can be tilted and/or angle-polished at the spectrometer entrance 916 similar to the first, second, and third embodiments (discussed above) so that the FFP peak direction of light delivered through the fundamental mode of the detection bundle of optical fibers 200 is not parallel to optical axis of the spectrometer 202 at the spectrometer entrance.

Figure 10:
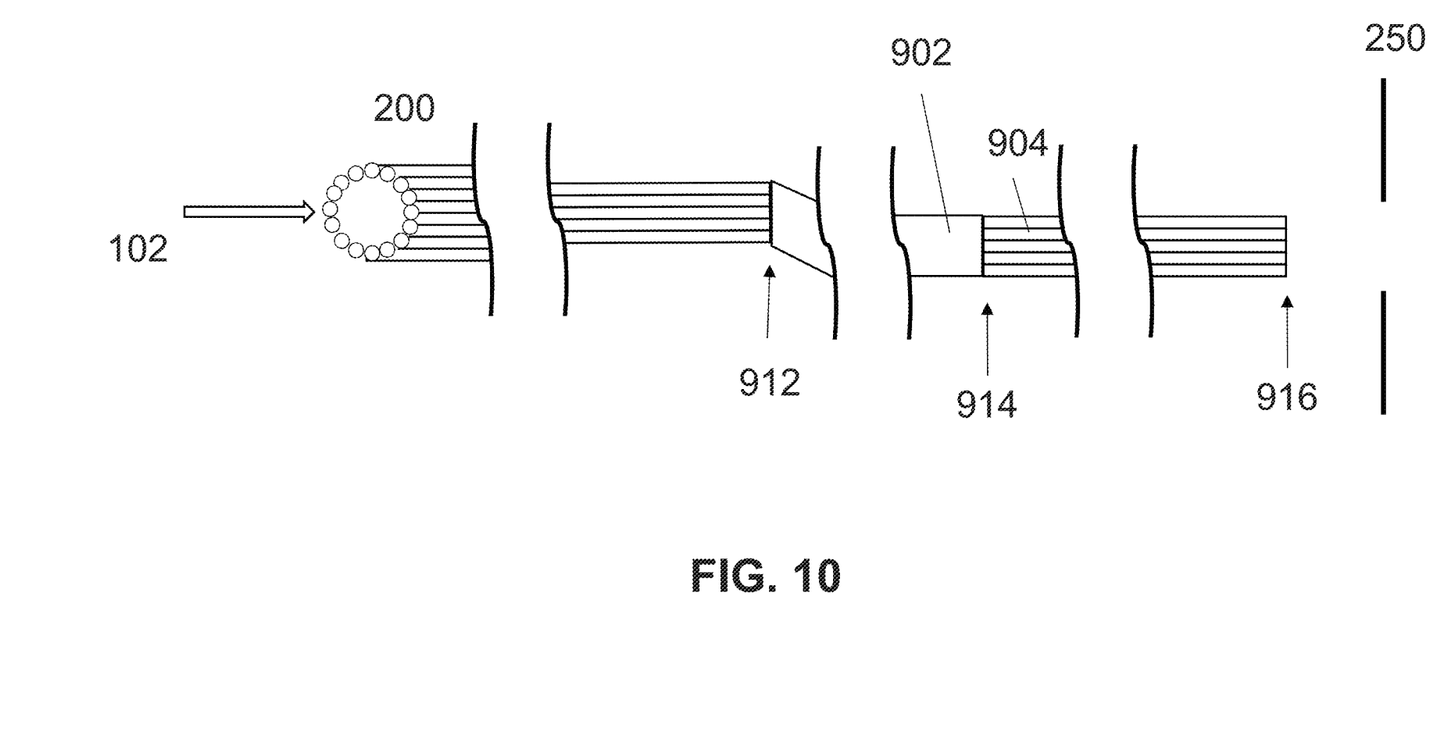
FIG. 10 is an exploded partial view of SEE detection optics having an angle polish feature at least one joint of end(s) of a bundle of optical fibers and/or end(s) of a waveguide(s), according to a fifth example embodiment of the present disclosure.

Referring now also to FIG. 10, there is shown an exploded partial view of SEE detection optics having an angle polish feature at least one of the optical fiber bundles/waveguide 200, 902 or 904 at the joint 912 or 914, according to a fifth example embodiment of the present disclosure. For example, at least one of the bundles of optical fiber optical fibers/waveguide 200, 902 or 904 can be angled at the joint 912 or 914, as shown in FIG. 10. This angling can be provided instead of the angling at the end at spectrometer entrance 916. In this case light delivered through the fundamental mode of the detection optical fiber bundle 200 will be coupled into high order mode of the optical fiber bundle 904 which is connected to the spectrometer 202. That is the FFP peak direction of light delivered through the fundamental mode of the detection optical fiber bundle 200 is not parallel to optical axis of the spectrometer 202 at the spectrometer entrance. On the other hand, some light delivered through high order mode of the detection optical fiber bundle 200 will be coupled into low order mode (including fundamental mode) of the optical fiber bundle 904. Alternatively, angling of at least one of the bundles of optical fiber optical fibers/waveguide 200, 902 or 904 can be provided at the joint 912 or 914 in addition to angling of the ends of optical fibers at the entrance of the spectrometer 916.

For example, the bundles of optical fiber optical fibers/waveguide 200, 902 or 904 in the embodiments above can be step-index fibers, gradient index fibers, photonic crystal fibers, or a combination of those fibers. For example, a fiber bundle end can be polished and/or fused.

Figure 11:
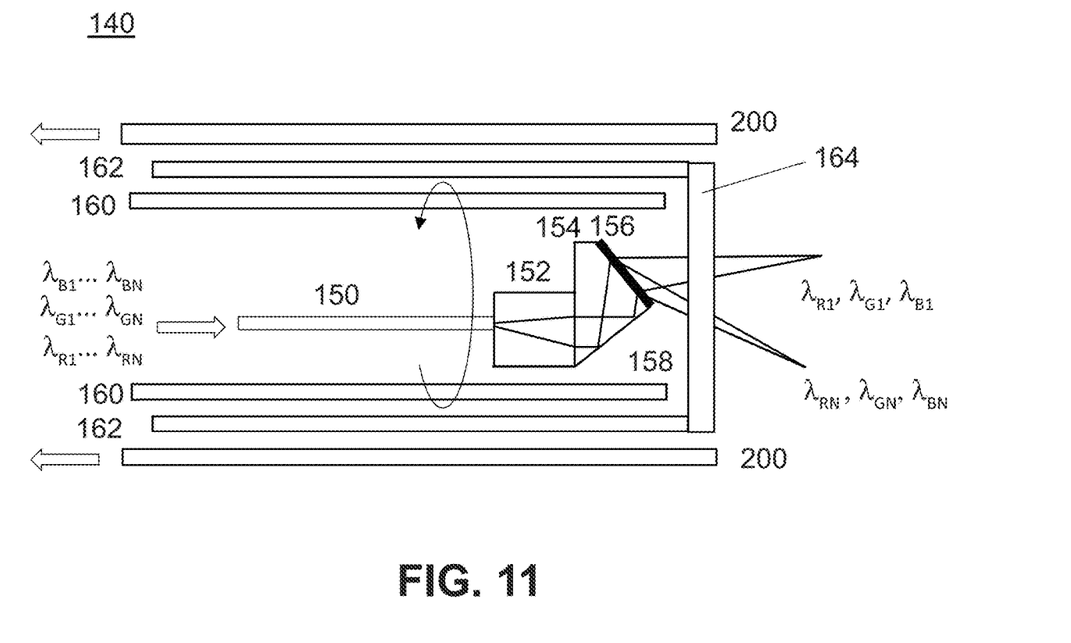
FIGS. 11, 12 and 13 are views of SEE detection optics having a high diffraction mode beneficial, for example, for suppressing ghost image(s), in accordance with a sixth example embodiment of the present disclosure.
Figure 12:
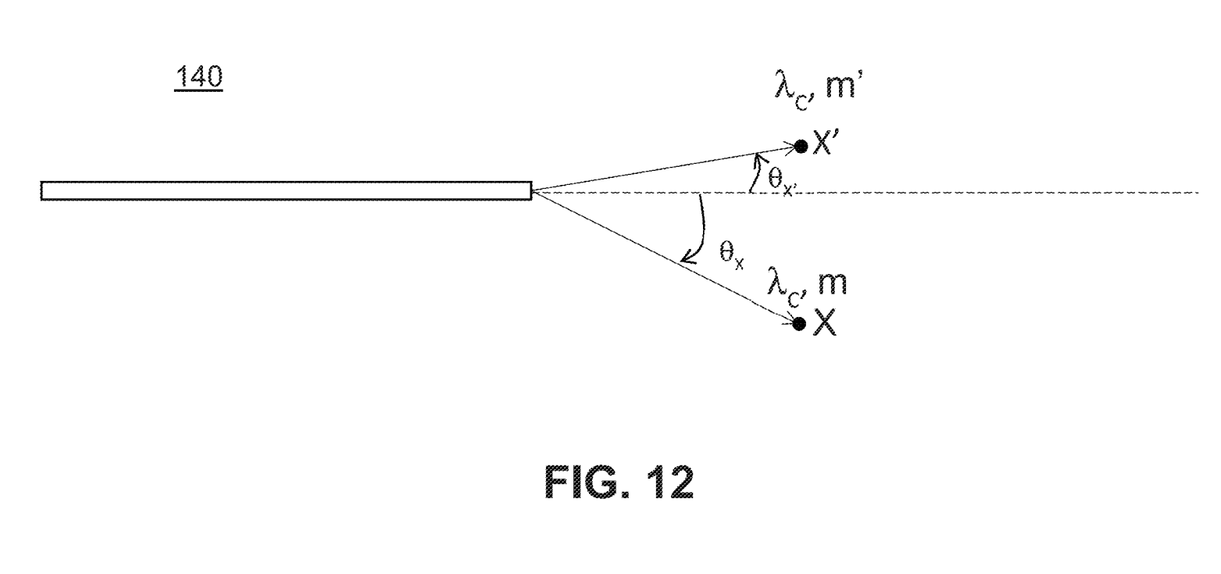
Figure 13:
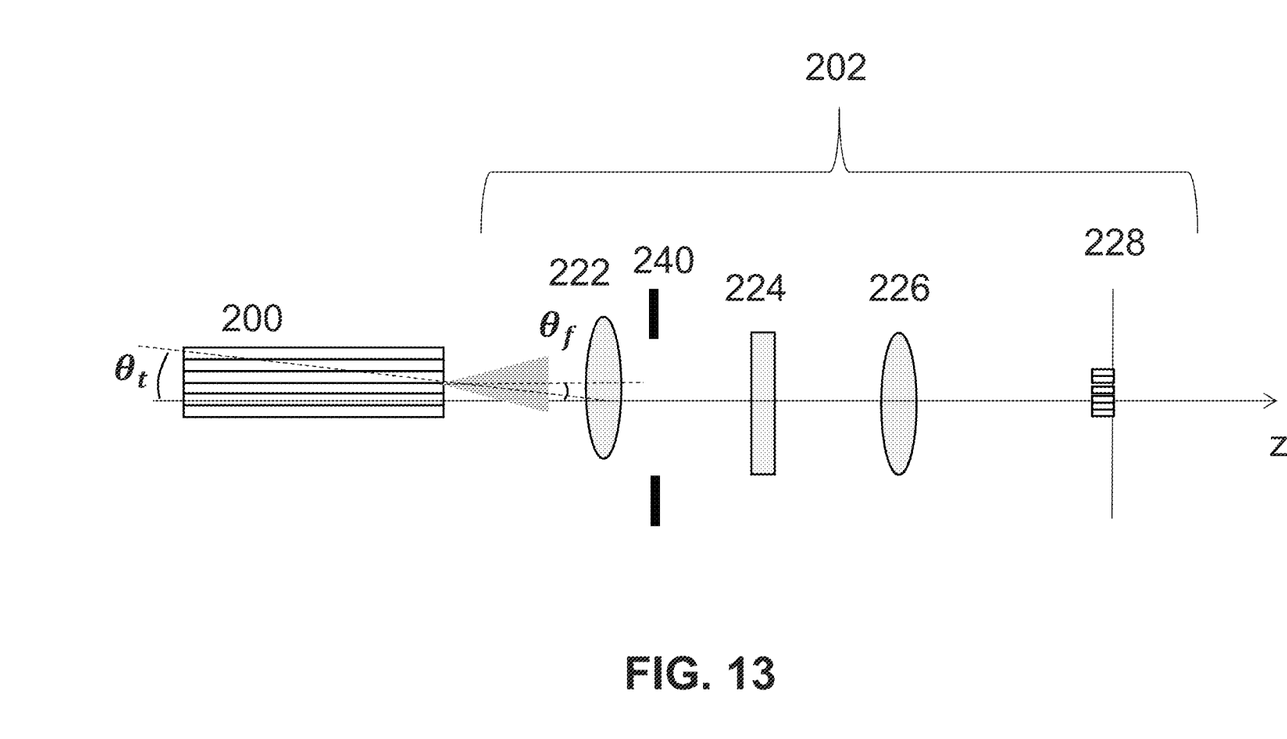

Referring now also to FIGS. 11, 12 and 13, there are shown views of SEE detection optics having a high diffraction mode beneficial, for example, for suppressing ghost image(s), in accordance with a sixth example embodiment of the present disclosure. FIG. 11 shows a schematic image of an example of SEE probe 140. Broadband light is coupled to a single mode optical fiber 150. The single mode optical fiber 150 is attached to a GRIN lens 152 and a spacer 154. The spacer 154 has a mirror surface 158 and a grating surface 156. The light from the single mode optical fiber 150 is focused by the GRIN lens 152, reflected by mirror 158 and diffracted by a diffraction grating 156. The optical fiber 150, GRIN lens 152, and spacer 154 are inside of the drive cable 160, and those are rotated inside of the sheath tubing 162. A window 164 is attached on the sheath tubing 162. Illumination light from the grating is focused on imaging target through the window 164. The detection optical fiber bundle 200 surrounds the sheath tubing 162.

To achieve color imaging, light of three wavelength ranges ($\lambda_{R1} \ldots \lambda_{RN}, \lambda_{G1} \ldots \lambda_{GN}, \lambda_{B1} \ldots \lambda_{BN}$) is diffracted in high order such as −4th, −5th, −6th order respectively, and focuses on an imaging target. Light of three wavelengths ($\lambda_{R1}, \lambda_{G1}, \lambda_{B1}$) is diffracted by the diffraction grating 156 in −4th, −5th, −6$^{th}$ orders respectively, and travels toward the imaging target. The detection optical fibers 200 detect light of those wavelengths ($\lambda_{R1}, \lambda_{G1}, \lambda_{B1}$) reflected by the imaging target. Probe diffraction efficiency is optimized for the view angle for those wavelengths and diffraction orders.

In such condition where multiple diffraction orders are used for spectrally-encoded illumination, there is illumination light which is not diffracted in appropriate order. For example, when light of wavelength $\lambda_C$ is diffracted in order of m and focuses on location X of the imaging target as shown in FIG. 12, same wavelength light can be diffracted in different order (lower order) m' and can focus on different location X'. The detection optical fiber may have a larger coupling efficiency for X', and the probe diffraction efficiency for X' may not be as low for wavelengths whose view angle $\theta_X$ of X is larger than the view angle $\theta_{X'}$ of X'. Accordingly, a signal from location X could be degraded by being mixed with false signal from location X' in image reconstruction process (generating ghost noise). However, in accordance with the present embodiment, such degradation is suppressed by combining with the previous embodiments so that the FFP peak direction of light delivered through the fundamental mode of the detection optical fiber bundle 200 is not parallel to optical axis of the spectrometer 202 at the spectrometer entrance. Moreover, although diffraction efficacy for X' is low for wavelengths whose $\theta_X$ is smaller than $\theta_{X'}$, such degradation is of small magnitude and insignificant.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., central processing unit (CPU), micro processing unit (MPU), or the like), and may include a network of separate computers or separate processors to read out and execute the computer executable instructions. The computer executable instructions may be provided to the computerized configuration(s), for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from U.S. Provisional Application No. 62/797,882, filed Jan. 28, 2019, which is hereby incorporated by reference herein in its entirety.

What is claimed is:

1. A spectrally encoded endoscopy optical device comprising:
a bundle of multi-mode optical fibers configured to transmit light received from an imaging target to a spectrometer, wherein a far field pattern of light transmitted through a fundamental mode of at least one of the multi-mode optical fibers is nonparallel to an optical axis of the spectrometer.

2. The spectrally encoded endoscopy optical device according to claim 1, wherein a far field pattern of light transmitted through a fundamental mode of the bundle of multi-mode optical fibers is nonparallel to an optical axis of the spectrometer.

3. The spectrally encoded endoscopy optical device according to claim 2, wherein the bundle of multi-mode optical fibers is tilted at an output end relative to the optical axis of the spectrometer.

4. The spectrally encoded endoscopy optical device according to claim 2, wherein the bundle of multi-mode optical fibers is tilted at an output end relative to the optical axis of the spectrometer, the output end disposed at an optical input of the spectrometer.

5. The spectrally encoded endoscopy optical device according to claim 2, wherein at least one of the multi-mode optical fibers has at least one of an input end and an output end that is angled relative to the optical axis of the at least one of the multi-mode optical fibers.

6. The spectrally encoded endoscopy optical device according to claim 2, wherein the multi-mode optical fibers are angle polished at least one of an input end and an output end.

7. The spectrally encoded endoscopy optical device according to claim 2, wherein the multi-mode optical fibers are angle polished at an output end that is both disposed at an optical input of the spectrometer and perpendicular to an optical axis of the spectrometer.

8. The spectrally encoded endoscopy optical device according to claim 2, further comprising:
an optical transmission medium disposed between the bundle of multi-mode optical fibers and the spectrometer, the optical transmission medium comprising at least one of an additional bundle of optical fibers and a waveguide.

9. The spectrally encoded endoscopy optical device according to claim 1, further comprising an illumination optical device that supplies illumination light to the target, wherein the multi-mode optical fibers are bundled to the illumination optical device and disposed to receive the illumination light reflected off the target and to transmit the received illumination light to the spectrometer.

10. The spectrally encoded endoscopy optical device according to claim 1, further comprising illumination optics that supplies illumination light to the target, wherein the multi-mode optical fibers are bundled to the illumination optics and disposed to receive the illumination light reflected off the target and to transmit the received illumination light to the spectrometer.

11. The spectrally encoded endoscopy optical device according to claim 10, wherein the multi-mode optical fibers are bundled together around the illumination optics so as to surround the optical axis of the illumination optics and serve as a spectrally encoded endoscopy optical probe.

12. The spectrally encoded endoscopy optical device according to claim 10, wherein the illumination optics supplies the illumination light to the target at a sufficiently high diffraction order to support color imaging.

13. The spectrally encoded endoscopy optical device according to claim 10, wherein the illumination optics supplies the illumination light to the target at least a fourth diffraction order.

14. The spectrally encoded endoscopy optical device according to claim 10, wherein the illumination optics supplies the illumination light to the target at least fourth, fifth, and sixth diffraction orders.

* * * * *